US009848598B2

(12) United States Patent
Frey et al.

(10) Patent No.: US 9,848,598 B2
(45) Date of Patent: *Dec. 26, 2017

(54) CRYOPROTECTED, FROZEN RECOMBINANT CANCER CELLS

(71) Applicant: ADURO GVAX INC., Berkeley, CA (US)

(72) Inventors: David Frey, Half Moon Bay, CA (US); Andy Lin, Palo Alto, CA (US); Gautum Banik, Foster City, CA (US)

(73) Assignee: ADURO GVAX INC., Berkeley, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/236,343

(22) Filed: Aug. 12, 2016

(65) Prior Publication Data

US 2016/0345574 A1 Dec. 1, 2016

Related U.S. Application Data

(63) Continuation of application No. 13/040,685, filed on Mar. 4, 2011, now Pat. No. 9,433,204, which is a continuation of application No. 11/484,954, filed on Jul. 12, 2006, now abandoned, which is a continuation of application No. 10/323,664, filed on Dec. 20, 2002, now Pat. No. 7,176,022.

(51) Int. Cl.

| | | |
|---|---|---|
| *C12N 5/00* | (2006.01) | |
| *A01N 1/02* | (2006.01) | |
| *A61K 35/407* | (2015.01) | |
| *A61K 38/19* | (2006.01) | |
| *A61K 39/39* | (2006.01) | |
| *A61K 47/20* | (2006.01) | |
| *A61K 47/36* | (2006.01) | |
| *A61K 47/42* | (2017.01) | |
| *A61K 35/12* | (2015.01) | |
| *A61K 48/00* | (2006.01) | |
| *A61K 39/00* | (2006.01) | |

(52) U.S. Cl.
CPC ............ *A01N 1/0221* (2013.01); *A01N 1/02* (2013.01); *A61K 35/407* (2013.01); *A61K 38/193* (2013.01); *A61K 39/0011* (2013.01); *A61K 39/39* (2013.01); *A61K 47/20* (2013.01); *A61K 47/36* (2013.01); *A61K 47/42* (2013.01); *A61K 35/12* (2013.01); *A61K 48/00* (2013.01); *A61K 2039/5152* (2013.01); *A61K 2039/55522* (2013.01); *Y10T 436/108331* (2015.01)

(58) Field of Classification Search
None
See application file for complete search history.

(56) References Cited

U.S. PATENT DOCUMENTS

| | | | |
|---|---|---|---|
| 4,004,975 A | 1/1977 | Lionetti et al. | |
| 5,364,756 A | 11/1994 | Livesey et al. | |
| 6,007,814 A | 12/1999 | Scheinberg | |
| 6,007,978 A | 12/1999 | Goodrich, Jr. et al. | |
| 6,464,973 B1 | 10/2002 | Levitsky et al. | |
| 6,852,537 B2 | 2/2005 | Hebbel et al. | |
| 7,176,022 B2* | 2/2007 | Frey ................ | A01N 1/02 435/1.3 |
| 7,250,291 B1* | 7/2007 | Dranoff ............ | C07K 14/4747 435/320.1 |
| 9,433,204 B2* | 9/2016 | Frey ................ | A01N 1/02 |
| 2002/0042130 A1 | 4/2002 | Hebbel et al. | |

FOREIGN PATENT DOCUMENTS

| | | |
|---|---|---|
| CA | 2158655 A1 | 9/1994 |
| EP | 0151030 A2 | 8/1985 |
| EP | 0198474 A1 | 10/1986 |
| EP | 1575643 B1 | 4/2013 |
| JP | 6255088 | 3/1987 |
| JP | 6315395 B2 | 11/1994 |
| JP | 8507921 | 8/1996 |
| JP | 2002531521 A | 9/2002 |
| WO | 9003183 A1 | 4/1990 |
| WO | 9106866 A2 | 5/1991 |
| WO | 9118505 A1 | 12/1991 |
| WO | 9306867 A1 | 4/1993 |
| WO | 9418995 A1 | 9/1994 |
| WO | 9724132 A1 | 7/1997 |
| WO | 0033870 A2 | 6/2000 |
| WO | 0033871 A2 | 6/2000 |

OTHER PUBLICATIONS

Ashwood-Smith et al., Low-temperature preservation of mammalian cells in tissue culture with polyvinylpyrrolidone (PVP), dextrans, and hydroxyethyl starch (HES). Cryobiology. Oct. 1972;9(5):441-449.
Atlas, Handbook of Microbiological Media. Second Edition, CRC Press, (1997)—in its entirety.
Ausubel et al., Short Protocols in Molecular Biology: A Compendium of Methods from Current Protocols in Molecular Biology. Fourth Edition, John Wiley & Sons. Inc. (1999)—in its entirety.
Berger and Kimmel, Guide to Molecular Cloning Techniques. Methods in Enzymology. vol. 152, Academic Press, Inc. (1987)—in its entirety.
International Search Report issued in PCT/US03/40822 dated Jun. 28, 2004.
Supplementary European Search Report issued in EP 03800054 dated Jun. 3, 2009.
Freshney, Culture of Animal Cells, A Manual of Basic Technique. Fourth Edition, Wiley-Liss, New York (2000)—in its entirety.
Gamborg and Phillips, Plant Cell, Tissue and Organ Culture, Fundamental Methods. Springer Lab Manual. Springer-Verlag Berlin Heidelberg New York (1995)—in its entirety.

(Continued)

*Primary Examiner* — Blaine Lankford
(74) *Attorney, Agent, or Firm* — Acuity Law Group, PC; Michael A. Whittaker

(57) ABSTRACT

This invention provides compositions and methods for cryoprotection of recombinant live cancer cells. Specifically, an improved cryoprotective medium is provided which includes a hydroxyethyl starch and/or derivative thereof alone or in combination with either DMSO or glycerol.

12 Claims, 7 Drawing Sheets

(56) References Cited

OTHER PUBLICATIONS

Gorlin, Stem Cell Cryopreservation. J Infus Chemother. 1996 Winter;6(1):23-27.
Isbell et al., Measurement of Cryoprotective Solvent Penetration into Intact Organ Tissues Using High-Field NMR Microimaging. Cryobiology. Sep. 1997;35(2):165-172.
Klein et al., Properties of the K562 cell line, derived from a patient with chronic myeloid leukemia Int J Cancer. Oct. 15, 1976;18(4):421-431.
Leibo et al., Effects of Freezing on Marrow Stem Cell Suspensions: Interactions of Cooling and Warming Rates in the Presence of PVP, Sucrose, or Glycerol. Cryobiology. Jan.-Feb. 1970;6(4):315-332.
Lozzio and Lozzio, Human Chronic Myelogenous Leukemia Cell-Line With Positive Philadelphia Chromosome. Blood. Mar. 1975;45(3):321-334.
Luo et al., Effect of Dimethylsulfoxide and Hydroxyethyl Starch in the Preservation of Fractionated Human Marrow Cells. Cryobiology. Aug. 1994;31(4):349-354.
Merten et al., A Simple Serum-free Freezing Medium for Serum-free Cultured Cells. Biologicals. Jun. 1995;23(2):185-189.
Odavic et al., Cryoprotection of Human Bone Marrow Committed Stem Cells (CFU-c) by Dextran, Glycerol and Dimethyl Sulfoxide. Experientia, 1980;36:1122-1124.
Ossowski and Belin, Effect of Dimethyl Sulfoxide on Human Carcinoma Cells, Inhibition of Plasminogen Activator Synthesis, Change in Cell Morphology, and Alteration of Response to Cholera Toxin. Mol Cell Biol. Dec. 1985;5 (12):3552-3559.
Payne et al., Plant Cell and Tissue Culture in Liquid Systems. Hanser Publishers (1992)—in its entirety.
Peters and Hanna, Active Specific Immunotherapy of Established Micrometastasis: Effect of Cryopreservation Procedures on Tumor Cell Immunogenicity in Guinea Pigs. J Natl Cancer Inst. Jun. 1980;64(6):1521-1525.

Sambrook and Russell, Molecular Cloning, A Laboratory Manual. Third Edition, Cold Spring Harbor Laboratory Press. vols. 1-3. Cold Spring Harbor, New York (2001)—in its entirety.
Selvan et al., Serum-Free Cryopreservation Solution for Storage of Tumor Cell Vaccine. J Immunother. 2000;23:600.
Shreffler et al., Standardization and performance evaluation of mononuclear cell cytokine secretion assays in a multicenter study. BMC Immunol. Dec. 12, 2006;7:29.
Sofrenovic et al., Circulating Angiogenic Cells can be Derived from Cryopreserved Peripheral Blood Mononuclear Cells. PLoS One. 2012;7(10):e48067.
Stiff et al., Autologous Bone Marrow Transplantation Using Unfractionated Cells Cryopreserved in Dimethylsulfoxide and Hydroxyethyl Starch Without Controlled-Rate Freezing. Blood. Oct. 1987;70(4):974-978.
Takahashi et al., Mechanism of Cryoprotection by Extracellular Polymeric Solutes. Biophys J. Sep. 1988;54(3):509-518.
Takaue et al., Comparative Analysis of Engraftment After Cryopreservation of Peripheral Blood Stem Cell Autografts by Controlled-Versus Uncontrolled-Rate Methods. Bone Marrow Transplant. Jun. 1994;13(6):801-804.
Venkataraman, Effects of Cryopreservation on Immune Responses. XI. Heightened Secretion of Tumor Necrosis Factor-alpha by Frozen Human Peripheral Blood Mononuclear Cells. Cryobiology. May 1997;34(3):276-283.
Wang et al., The Influence of Cryopreservation on Cytokine Production by Human T Lymphocytes. Cryobiology. Aug. 1998;37(1):22-29.
Yoshida and Takeuchi, Primary culture and cryopreservation of mouse astrocytes under serum-free conditions. Cytotechnology. Feb. 1991;5(2):99-106.

* cited by examiner

CRYOPROTECTED, FROZEN RECOMBINANT CANCER CELLS

CROSS-REFERENCE TO RELATED APPLICATIONS

This application is a continuation of U.S. patent application Ser. No. 13/040,685, filed Mar. 4, 2011, now issued as U.S. Pat. No. 9,433,204, which is a continuation of U.S. patent application Ser. No. 11/484,954, filed Jul. 12, 2006, now abandoned, which is a continuation of U.S. patent application Ser. No. 10/323,664, filed Dec. 20, 2002, now issued as U.S. Pat. No. 7,176,022, each of which is hereby incorporated in its entirety including all tables, figures and claims.

FIELD OF THE INVENTION

The invention relates to compositions and methods for the cryopreservation of cellular vaccines. More specifically, the invention relates to the use of particular compositions comprising cryoprotective media that includes hydroxyethyl starch (HES) and glycerol or DMSO together with recombinant live cancer cells. The compositions can be frozen and thawed, when desired, for use as a cellular vaccine for the treatment of cancer.

BACKGROUND OF THE INVENTION

At certain periods of time in a tumor's cell growth, the patient's immune system has the ability to recognize the growth as abnormal (or non-self). As a result, various methods have been developed which take advantage of the patient's own immune system to fight cancer. Exemplary methods include the use of polyclonal and monoclonal antibodies, non-specific immune system stimulants, such as cytokines, protein or peptide subunit vaccines (e.g., using antigens that are often associated with cancer cells, such as tumor-specific antigens and tumor-associated antigens), adoptive immunotherapy or cellular therapy, gene therapy, cellular vaccines, etc. See, e.g., WO 00/3387.

Cellular vaccines wherein cells (or derivatives thereof) are the therapeutic agent are currently in clinical testing for treatment of cancer. Such cellular vaccines provide advantages over isolated protein vaccines in that whole cells are the vehicle for a broad range of antigens, e.g., on the cell surface. See, for example, Dranoff et al. WO 93/06867, Gansbacher et al., WO 94/18995, Jaffee et al, WO 97/24132, Mitchell et al. WO 90/03183 and Morton et al WO91/06866, each of which is expressly incorporated by reference herein.

Cells for use in such cellular vaccines can be modified, e.g. to express a protein which modulates the immune response to the cell. For example, a gene encoding a cytokine or costimulatory molecule may be introduced into cells derived from, e.g., a primary tumor taken from a patient, to create recombinant cancer cells. When the cytokine or costimulatory molecule is expressed, it is capable of modulating the immune response to the cell. The recombinant cancer cells may be expanded in vitro, treated to prevent further growth and returned to the patient. Appropriate timing of administration(s) and good cell viability are required for effective treatment with a cellular vaccine. Thus, it is important to be able to store recombinant cancer cells for use at selected time points, appropriate to particular treatments. Storage and maintenance of viability are important in order to allow for transportation, to decrease the amount of cell divisions the cells undergo before use in treatment and to ensure that an adequate and reproducible dose is delivered to the patient.

Freezing of cell compositions with maintenance of viability has been the subject of considerable research. Maintenance of cell viability following freezing and thawing continues to be a challenge. In the freezing process as the liquid component of a cell is changed to a solid, ice crystals are formed and damage can occur to the cells. At least two types of damage to cells is possible when ice crystals are formed. Rapid growth of ice crystals may physically disrupt membranes and subcellular organelles and may even lyse cells. Slow growth of ice crystals may result in cellular dehydration (because of the exclusion of electrolytes from the ice crystals) and extra-cellular ice formation. See, e.g., Gorlin, (1996) Journal of Infusional Chemotherapy, 6(1):23-27.

In an attempt to minimize the effects of ice crystal formation, cells are typically frozen in medium with cryoprotectants. Cryoprotectants protect the cells during freezing in a variety of ways. Collagiative cryoprotectants penetrate the cell and decrease the osmotic gradient across membranes. Vitrifying cryoprotectants increase the glass formation of the solution thereby creating a glass wall around the cell, which prevents dehydration. Cryoprotectants can also work by inhibiting ice crystal formation. See, e.g., Gorlin, (1996) Journal of Infusional Chemotherapy, 6(1):23-27.

Different cell types vary in their permeability to water and in their sensitivity to solute concentration. Leibo et al., (1970) Cryobiology, 6(4): 315-332. As a result, different types and combinations of cryoprotectants have been found to be effective to preserve specific types of cells. For example, human bone marrow committed stem cells have been shown to be preserve by a cryoprotectant combination of dextran, glycerol, and dimethyl sulfoxide (Odavic et al: (1980) Experienta 36:1122-1124), and mouse marrow stem cells have been shown to be preserved by polyvinylpyrolidone (PVP), sucrose or glycerol. See, e.g., Stiff et al. (1987) Blood, 70(4): 974-978; Venkataraman, (1997) Cryobiology, 34:276-283; Wang et al., (1998) Cryobiology, 37:22-29: Merten et al., (1995) Biologicals, 23:185-189; and, Yoshida and Takeuchi, (1991) Cytotechnology 5:99-106. Polymers, such as hydroxyethyl starch (HES), have been used to cryoprotect human monocytes and unfractionated cells for use in bone marrow transplantation. See, e.g., Takashi et al., (1988) Biophysical Journal, 54:509-518; and Stiff et al. (1987) Blood, 70(4): 974-978.

Cryoprotective media for cellular vaccines has not been reported. Thus, there remains a need for cryoprotective media and procedures that can be used to successfully preserve cellular vaccines for use as therapeutic agents. In view of the above, materials and methods that would provide for successful preservation and recovery of cells with a high percentage viability following freezing and thawing would be highly desirable for use in cellular vaccines. The present invention addresses this need, as will be apparent from the detailed description provided herein.

SUMMARY OF THE INVENTION

The invention provides compositions and methods that include cryoprotective media and recombinant live cancer cells for protecting and preserving the cells during freezing and thawing. The cryoprotective medium includes a hydroxyethyl starch (HES) or derivative thereof alone or combination with DMSO or glycerol.

Compositions of the invention include a recombinant live cancer cell in a cryoprotective medium comprising about 5% by weight to about 22% by weight of a hydroxyethyl starch (HES) or derivative thereof alone or in combination with about 1% by weight to about 15% by weight of DMSO or glycerol, and, optionally, from about 0% by weight to about 10% by weight human serum albumin (HSA).

A composition can include about 8% by weight of HES or a derivative thereof and about 5% by weight of DMSO or glycerol, and, optionally, about 2% by weight human serum albumin (HSA).

The HES of the invention can include a variety of molecules. For example, HES molecules can be: (a) etherified with hydroxyethyl groups wherein the degree of molecular substitution is from about 0.60-0.80; (b) etherified with hydroxyethyl groups, wherein the degree of molecular substitution is from about 0.40-0.60; or a combination of (a) and (b). Other examples of HES, include, but are not limited to HES molecules that are: (a) etherified with hydroxyethyl groups wherein the degree of molecular substitution is about 0.70; (b) etherified with hydroxyethyl groups, wherein the degree of molecular substitution is from about 0.4 to about 0.5; or a combination of (a) and (b). In one embodiment, HES includes a molecule with (a) a molecular weight of from about 420 to about 480 kDa; (b) a molecular weight of from about 200 to about 290 KM; or a combination of (a) and (b).

Many types of recombinant live cancer cells, such as patient-derived tumor cells, autologous cells, allogeneic cells and bystander cells, respectively, can be used in practicing the invention. Typically, a recombinant live cancer cell for use in practicing the invention comprises an introduced heterologous nucleic acid coding sequence or gene for a cytokine or costimulatory molecule.

Methods for preserving viability of recombinant live cancer cells are also included within the invention. Such methods include obtaining a plurality of recombinant live cancer Cells, concentrating the cells, suspending the cells in a cryoprotective medium such as described above, thereby providing a suspension and freezing the suspension to a cryogenic frozen state, thereby providing a frozen suspension. After thawing of the suspension to a liquid state at least about 60%, about 65%, about 70%, about 75% or more of the recombinant live cancer cells remain viable In one embodiment, the recombinant live cancer cells are irradiated prior to freezing or in the cryogenic frozen state, wherein the suspension is frozen at a temperature from about −200.degree. C. to a temperature of about −35.degree. C. The methods further include thawing the frozen suspension and administering the thawed suspension to a subject. Optionally, the thawed suspension is not washed prior to the administering step.

The invention further includes a frozen or thawed suspension prepared by a method described herein.

Kits for preserving cell viability are also included in the invention. Kits of the invention include: a container containing a cryoprotective medium such as described above and instructional materials teaching the use of the cryoprotective medium to preserve cell viability.

DETAILED DESCRIPTION

Figure 1:
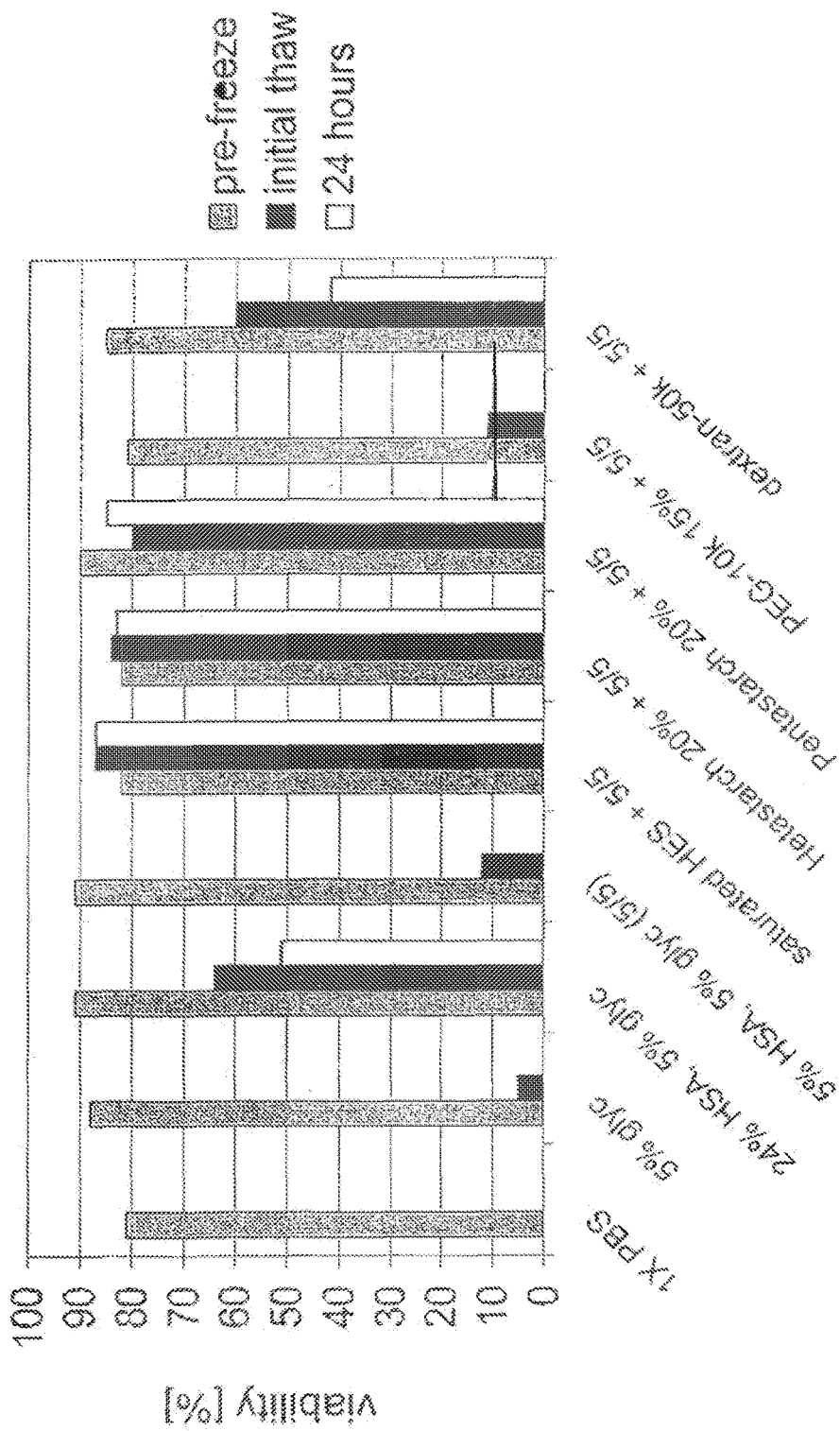
FIG. 1 is a graph showing the % viability of LNCaP cells before (pre-freeze), immediately after (initial thaw) and 24 hours after the cells were suspended in cryoprotective media, frozen to −80.degree. C. and thawed at 37.degree. C. The cryoprotective media tested was as follows: 1.times.PBS alone; 5% glycerol alone; 24% HSA, 5% glycerol; 5% HSA, 5% glycerol; saturated HES in 5% glycerol/5% HSA/PBS; 20% Hetastarch in 5% glycerol/5% HSA/PBS; 20% Pentastarch in 5% glycerol/5% HSA/PBS; 15% PEG (10K) in 5% glycerol/5% HSA/PBS; Dextran 50K in 5% glycerol/5% HSA/PBS.

There are many benefits to freezing cells in multiple aliquots and preserving their viability when thawed. For example, the frozen cells can be stored and/or transported for future use, e.g., for treatment, such as a cellular vaccine. However, freezing cells and preserving their viability is not a simple matter. Cell types differ in their permeability to water and in their sensitivity to solute concentration, thus, different types and combinations of cryoprotectants are needed to preserve specific types of cells. The invention provides composition and methods for preserving the viability of recombinant cancer cells using a cryoprotective medium that includes a hydroxyethyl starch (HES) or a derivative thereof alone or in combination with DMSO or glycerol.

Definitions

Unless defined otherwise, all scientific and technical terms are understood to have the same meaning as commonly used in the art to which they pertain. It is to be understood that this invention is not limited to the particular methodology, protocols, and reagents described, as these may vary. For the purpose of the present invention, the following terms are defined below.

The term "autologous" refers to cancer cells derived from an individual or primary descendents of those cells, wherein the cells may be used as a cellular vaccine for that same individual.

The term "allogeneic" as used herein refers to cancer cells of the same type being harbored by an individual, but established from a cancer cell line derived from an unrelated individual. Alternatively, an allogeneic cancer cell line is derived from an unrelated tumor type to the tumor harbored by an individual, but which shares common tumor associated antigens with the tumor of that individual. In general, allogeneic refers to genetic differences within a species, that is, differences between individuals of the same species. It follows that allogeneic cells for use as a cellular vaccine are genetically dissimilar to those of the individual to which they are administered.

The term "bystander" as used herein refers to a mammalian cell line, preferably a human cell line, which naturally lacks major histocompatibility class I (MHC-I) antigens and major histocompatibility class II (MHC-II) antigens or is modified so that it lacks MHC-I antigens and MHC-II antigens. Theoretically, any mammalian, preferably human, cell line that is capable of paracrine production of a cytokine or costimulatory molecule can be used. An exemplary bystander cell line is K562 (ATCC CCL-243; Lozzio et al., (1975) Blood 45(3): 321-334; Klein et al. (1976) Int. J. Cancer 18: 421-431). Heterologous nucleic acids or genes that encode a cytokine or costimulatory molecule may be introduced into bystander cells, and they may be mixed with cancer cells for use in a cellular vaccine.

By "introduced" is meant the provision to an autologous, allogeneic or bystander cell line of a nucleic acid molecule, e.g., a vector, that comprises a heterologous nucleic acid coding sequence or gene for a cytokine or costimulatory molecule that either is not expressed in the cell line or, as a result of the provision of the nucleic acid molecule, is now expressed at a greater level. A "vector" encompasses a DNA molecule, such as a plasmid, virus or other vehicle, which contains one or more heterologous or recombinant DNA sequences, e.g., a cytokine or costimulatory molecule gene or coding sequence of interest, under the operative control of a functional promoter and in some cases an enhancer as well. By recombinant or heterologous with reference to a vector or other DNA sequences merely acknowledges the linkage of DNA sequences which are not typically conjoined as found in nature.

The term "patient-derived tumor cells" refers to cells that have been recovered from a tumor taken from a patient. Typically a cell suspension is created from the isolated tumor. When used as a cellular vaccine, patient-derived tumor cells are treated in a manner effective to stop further replication, i.e. the cells are irradiated.

The term "recombinant cancer cell" refers to a cancer cell in which a heterologous nucleic acid coding sequence or gene for a cytokine or costimulatory molecule have been introduced.

The term "vaccine", as used herein refers to a cellular composition (e.g., a recombinant live cancer cell) for administration to a patient as part of a therapeutic regimen for the treatment of cancer. The vaccine typically contains cancer cells, some or all of which have been genetically modified to express a cytokine or other costimulatory molecule.

The term "cryogenic frozen state" refers to a temperature at which the cells can be frozen and/or stored for a desired length of time. For example a cryogenic frozen state can refer to a temperature, e.g., from about −200.degree. C. to a temperature of about −35.degree. C., from about −180.degree. C. to a temperature of about −35.degree. C., from about −150.degree. C. to a temperature of about −35.degree. C., from about −200.degree. C. to a temperature of about −50.degree. C., from about −200.degree. C. to a temperature of about −60.degree. C. and the like.

The term "cryoprotective medium" refers to the medium in which cells are suspended when frozen and/or thawed. For example, the cryoprotective medium described herein includes a hydroxyethyl starch (HES) or derivative thereof alone or in combination with DMSO or glycerol. The cryoprotective medium can also include human serum albumin (HSA). The term "cryoprotective medium" may be used interchangeably with the terms "cryo-protecting formulation" and "cryoprotective formulation". The components of the "cryoprotective medium" may be described herein as "polymers".

The terms "nucleic acid" or "oligonucleotide" or grammatical equivalents herein refer to at least two nucleotides or analogues thereof, covalently linked together. A nucleic acid of the invention is typically single-stranded or double stranded and will generally contain phosphodiester bonds, although in some cases, nucleic acid analogs are included that can have alternate backbones, comprising, for example, phosphoramide; phosphorothioate, O-methylphophoroamidite linkages or peptide nucleic acid backbones and linkages. The depiction of a single strand also defines the sequence of the other strand and thus also includes the complement of the sequence.

The term "hydroxyethyl starch" or "HES", as used herein refers to a polymer of hydroxyethyl starch or a derivative thereof, which exhibits the same properties as a cryoprotectant as HES itself. HES of the invention can include a variety of molecules, as further described below.

The term "patient" as used herein may refer to any mammal. The invention is useful for both the human and other mammalian subjects.

Cryoprotective Medium

The invention provides cryoprotective formulations for preserving the viability of recombinant live cancer cells during freezing to a cryogenic frozen state and thawing to a liquid state. These preserved recombinant live cancer cells can be used, when desired, as cellular vaccines, e.g., for the treatment of cancer.

Cryoprotective medium of the invention includes at least one cryoprotectant, such as, hydroxyethyl starch (HES), and often includes other cryoprotectants as well, e.g., DMSO, or glycerol, and optionally human serum albumin (HSA). In one embodiment, the cryoprotective medium of the invention can be free or substantially free of human serum albumin (HSA). Since HSA is a human-derived material, elimination of this excipient can reduce the potential risk of contamination of cellular product with adventitious agents.

The cryoprotective medium of the invention includes a polymer, hydroxyethyl starch (HES). HES has typically found use as a plasma expander. Hetastarch, the most common hydroxyethyl starch, is derived from corn starch and has a molecular weight of about 450,000 daltons. Pentastarch is an analog of Hetastarch with a molecular weight of about 264,000 daltons. The HES of the invention includes a variety of molecules. For example, HES can comprise HES molecules that are (a) etherified with hydroxyethyl groups where the degree of molecular substitution is from about 0.60-0.80; (b) etherified with hydroxyethyl groups, wherein the degree of molecular substitution is from about 0.40-0.60; or a combination of (a) and (b). Other examples of HES, include, but are not limited to, HES that is, e.g., (a) etherified with hydroxyethyl groups where the degree of molecular substitution is about 0.70; (b) etherified with hydroxyethyl groups, where the degree of molecular substitution is from about 0.4 to about 0.5; or a combination of (a) and (b). In one embodiment, HES includes a molecule with (a) a molecular weight of from about 420 to about 480 kDa; (b) a molecular weight of from about 200 to about 290 kDa; or a combination of (a) and (b). For example, HES can include Hetastarch (B. Braun-McGaw) and/or Pentastarch (B. Braun-McGaw).

HES has been used as a protective agent for the cryopreservation of erythrocytes and platelets and when combined with DMSO. See, e.g., Ashwood-Smith et al. (1972) Cryobiology 9:441-449.

Dimethylsulfoxide (DMSO) or glycerol are also optionally used in the cryoprotective media of the invention. While the mechanism is not part of the invention, DMSO and glycerol can act by decreasing the osmotic gradient across membranes. These agents maintain an increased volume of cellular solution and exert colligative (depending on the number of particles (and not on the nature of the particles) action within the cells. This avoids an excessive concentration of toxic electrolytes in the non-frozen cellular solution. If there is enough protective agent compound, the salt concentration does not rise to a critically damaging level until the temperature becomes so low that the damaging reactions are slow enough to be tolerated by the cells.

In one aspect, a composition of the invention includes a recombinant live cancer cell in a cryoprotective medium, wherein the cryoprotective medium comprises a hydroxyethyl starch (HES) or derivative thereof alone or in combination with DMSO. In one embodiment, the composition includes about 5% by weight to about 22% by weight of HES or a derivative thereof and about 1% by weight to about 15% by weight of DMSO, and, optionally, from about 0% by weight to about 10% by weight human serum albumin (HSA).

In another embodiment, a composition can include about 5% by weight to about 15% by weight of HES or a derivative thereof and about 1% by weight to about 10% by weight of DMSO, and, optionally, from about 0% by weight to about 10% by weight human serum albumin (HSA). In another embodiment, a composition can include about 5% by weight to about 10% by weight of HES or a derivative thereof and about 1% by weight to about 6% by weight of DMSO, and, optionally, from about 0% by weight to about 10% by weight human serum albumin (HSA). For example, in one preferred embodiment, a composition of the invention includes a recombinant live cancer cell in a cryoprotective medium comprising a final percentage of about 8% by weight HES, about 2% by weight HSA, and about 5% by weight DMSO. HES may include Pentastarch, Hetastarch, a combination or derivative thereof.

Compositions of the invention also include a recombinant live cancer cell in a cryoprotective medium, wherein the cryoprotective medium comprises a hydroxyethyl starch (HES) or derivative thereof alone or in combination with glycerol. In one embodiment, a composition includes about 5% by weight to about 22% by weight of the HES or derivative thereof and about 1% by weight to about 15% by weight of the glycerol, and, optionally, from about 0 to about 10% human serum albumin (HSA). In another embodiment, a composition includes about 5% by weight to about 15% by weight of the HES or derivative thereof and about 1% by weight to about 10% by weight of the glycerol, and, optionally, from about 0 to about 10% human serum albumin (HSA). In yet another embodiment, a composition includes about 5.degree. A) by weight to about 10% by weight of the HES or derivative thereof and about 1% by weight to about 6% by weight of the glycerol, and, optionally, from about 0 to about 10% human serum albumin (HSA). For example, in another preferred embodiment, a composition of the invention includes a recombinant live cancer cell in a cryoprotective medium comprising a final percentage of about 8% by weight HES, about 2% by weight HSA, and about 5% by weight glycerol. HES may include Pentastarch, Hetastarch, a combination or derivative thereof.

A cryoprotective medium of the invention is typically diluted in a solution, which is at a physiological pH. Exemplary solutions for use in practicing the invention include, but are not limited to phosphate buffered saline (PBS), Dulbecco's Modified Eagle's Medium (DMEM), IDMEM, MEM, RPMI 1640, Ham's F-12, Normosol R, lactated Ringer's, Hank's balanced salt solution (HBSS), and combinations thereof. In addition, the cryoprotective medium can contain auxiliary substances, such as, water, saline, pH buffering agents, carriers or excipients, other stabilizers and/or buffers or other reagents that enhance the viability and/or cytokine or other costimulatory molecule expression of the recombinant live cancer cells following the freezing and thawing process.

Typically, the cell suspension is frozen at a temperature of from e.g., from about −200.degree. C. to a temperature of about −35.degree. C., from about −180.degree. C. to a temperature of about −35.degree. C., from about −150.degree. C. to a temperature of about −35.degree. C., from about −200.degree. C. to a temperature of about −50.degree. C., from about −200.degree. C. to a temperature of about −60.degree. C. and the like. In one embodiment, frozen cells are stored at a temperature below which any recrystallization can occur, e.g., the temperature below the glass transition of pure water (e.g., less than about −135.degree. C.). Standard methods known in the art are used to freeze the cells, e.g., containers holding a cryoprotective medium of the invention and recombinant cells can be immersed in, a solid carbon dioxide and alcohol mixture, or in liquid nitrogen. The containers can also be placed directly in a freezer, which is set at a desired temperature, e.g., about equal to or less than about −35.degree. C. Cryogenic equipment can also be used, e.g., a programmed freezer or rate-controlled freezer (CryoMed, Mt. Clemens, Mich. or UTL-80, Neslab Instruments Inc., Portsmouth, N.H.). The frozen cells are typically transferred to a freezer, which is set at a desired temperature, e.g., about equal to or less than about −35.degree. C. Liquid nitrogen (the liquid and/or gas phase) can also be used to freeze and store the cells. Other freezing methods and apparatus known in the art can also be used in practicing the methods described herein.

Methods for preserving viability of recombinant live cancer cells upon freezing and thawing are included in the invention. An exemplary method includes the steps of obtaining a plurality of recombinant live cancer cells (e.g., mammalian cells, such as lung cancer cells, pancreatic cancer cells, prostate cancer cells, kidney cancer cells, myeloma cells, leukemic cells and the like); concentrating the plurality of recombinant live cancer cells using standard procedures routinely employed in the art; suspending the recombinant live cancer cells in a cryoprotective medium comprising a HES or a derivative thereof alone or in combination with DMSO and from about 0% by weight to about 10% by weight human serum albumin (HSA), thereby providing a suspension. The suspension is frozen to a cryogenic frozen state, thereby providing a frozen suspension, where following thawing of the suspension to a liquid state at least about 60%, 65%, 70%, 75% or more of the recombinant live cancer cells remain viable. In one approach, the recombinant live cancer cells are irradiated (e.g., irradiated prior to freezing or irradiated in the cryogenic frozen state). Typically, the frozen suspension is frozen at a temperature of from about −200.degree. C. to a temperature of about −35.degree. C.

The recombinant cancer cells are typically expanded in vitro, treated to render the cells proliferation-incompetent and returned to the patient. In one embodiment, the cells are rendered proliferation-incompetent by irradiation. Typically, the cells are plated in a tissue culture plate and irradiated at room temperature using a Cs source and irradiated at a dose rate of from about 50 to about 200 rads/min, preferably, from about 120 to about 140 rads/min. In a preferred approach, the cells are irradiated with a total dose sufficient to inhibit the majority of cells from proliferating in vitro. Thus, desirably the cells are irradiated with a total dose of from about 10,000 to 20,000 rads, optimally, with about 15,000 rads, such that 100% of the cells are rendered proliferation-incompetent.

In one embodiment, a frozen suspension prepared a method described herein is included in the invention. In another embodiment, a thawed suspension prepared by a method described herein is included in the invention.

In one embodiment, the methods further include thawing the frozen suspension thereby providing a thawed suspension and administering the thawed suspension to a subject. Optionally, the thawed suspension is not washed prior to the administering step.

Thawing can take place by allowing samples to thaw slowly at, e.g., room temperature, or by immersing frozen samples in liquid, e.g., water, at a set temperature, e.g., about 37.degree. C. Cells can also be thawed by mixing the cells with thawed medium. Optionally, cells can be thawed using a programmed freezer.

In one embodiment, the plurality of recombinant live cancer cells are autologous or allogeneic and further comprise an introduced heterologous nucleic acid coding sequence for a cytokine or costimulatory molecule, e.g., granulocyte-macrophage colony stimulating factor (GM-CSF). In another embodiment, the recombinant live cancer cells are bystander cells, and the method further comprises thawing the frozen suspension, thereby providing a thawed suspension; providing patient-derived tumor cells, mixing the thawed suspension with patient-derived tumor cells (e.g., irradiated tumor cells), thereby providing a mixed suspension and administering the mixed suspension to a subject.

Methods of the invention obtaining a plurality of recombinant live cancer cells (e.g., autologous cells, allogeneic cells, bystander cells and the like); concentrating the plurality of recombinant live cancer cells; suspending the plurality of recombinant live cancer cells in a cryoprotective medium, comprising about 8% by weight of HES or a derivative thereof, about 2% by weight HSA and about 5% by weight DMSO, thereby providing a suspension; freezing the suspension to a cryogenic frozen state, thereby providing a frozen suspension; and irradiating the plurality of live recombinant cancer cells or the frozen suspension, where following thawing of the suspension to a liquid state at least about 60%, about 65%, about 70%, about 75% or more of the recombinant live cancer cells remain viable. In one embodiment, the method further includes thawing the frozen suspension, thereby providing a thawed suspension and administering the thawed suspension to a subject where the thawed suspension is not washed prior to the administering step. A thawed suspension prepared by this method is also included in the invention.

Following freezing and thawing, the thawed recombinant live cancer cells are returned, delivered, or transferred to the subject. The cells may be delivered to the tissue site from which they were obtained or to another site appropriate to the therapeutic regimen. If desired, the cells can be grafted onto a tissue, skin, organ, or body system of interest in the subject using standard and well-known grafting techniques or delivered to the blood or lymphatic system using standard delivery or transfusion techniques. Such delivery, administration, or transfer of thawed recombinant live cancer cells are typically made by using one or more of the routes or modes of administration described herein and know in the art. In one aspect, the amount of thawed recombinant live cancer cells administered is sufficient and effective to treat the disease or condition at the site or tissue system. The thawed recombinant live cancer cells can be administered, for example, intramuscularly, intradermally, subdermally, subcutaneously, orally, intraperitoneally, intrathecally, intravenously, or placed within a cavity of the body (including, e.g., during surgery), or by inhalation or vaginal or rectal administration.

Typically, the thawed recombinant live cancer cells (s) are administered in an amount sufficient to induce or reduce a desired phenotype, i.e., an "effective amount". Single or multiple administrations of the thawed recombinant live cancer cells can be carried out as needed. The subject can be at any stage of development at the time of administration, e.g., embryonic, fetal, infantile, juvenile or adult.

Recombinant Cancer Cells

The recombinant live cancer cells used in practicing the invention find utility in active immunotherapy which involves the injection of cancer or tumor cells in vivo to generate either a novel or an enhanced immune response thereto. The tumor cells employed can be patient-derived tumor cells (autologous or allogeneic), or bystander cells. Many types of recombinant live cancer cells find use in practicing the invention. Typically, the recombinant live cancer cells include an introduced heterologous nucleic acid coding sequence or gene for a cytokine or costimulatory molecule. Exemplary cytokines or costimulatory molecules include, but are not limited to, any molecule which is involved with the initiation, enhancement, strengthening, heightening, and/or lengthening of an immune response. In some embodiments, the cytokine or costimulatory molecule is GM-CSF, IL-1, IL-2, IL-3, IL-4, IL-6, IL-7, IL-10, CD2, IL-12, IL-15, IL-18, TGF, B7, MIP-1a, MIP-1p, MIP-2, M-CSF, G-CSF, and/or ICAM. In one preferred embodiment, the cytokine is GM-CSF. In other embodiments, more than one cytokine or costimulatory molecule is expressed by a recombinant live cancer cell of the invention.

In one embodiment, a heterologous nucleic acid coding sequence or gene is introduced into a cancer cell, e.g., a lung cancer cell, a pancreatic cancer cell, a prostate cancer cell, a kidney cancer cell, a myeloma cell, a leukemic cell and the like. Various methods can be employed for delivering a nucleic acid molecule, e.g., a vector, to a cell in vitro or ex vivo. Live cancer cells of the invention are typically genetically engineered (e.g., transformed, transduced or transfected) with a heterologous nucleic acid coding sequence. Many approaches for introducing nucleic acids into cells are known in the art. Such methods include electroporation, membrane fusion with liposomes (lipofection), high velocity bombardment with DNA, calcium phosphate mediated transfection, DEAE-dextran mediated transfection, infection with viral vectors, by use of polycation compounds such as polylysine, receptor specific ligands direct microinjection into single cells, spheroplast fusion whereby *E coli* containing the nucleic acid molecules are stripped of their outer cell walls and fused to animal cells using polyethylene glycol and the like. See, Berger and Kimmel, Guide to Molecular Cloning Techniques, Methods in Enzymology volume 152 Academic Press, Inc., San Diego, Calif. ("Berger"), Sambrook et al., Molecular Cloning—A Laboratory Manual (3rd Ed.), Vol. 1-3, Cold Spring Harbor Laboratory, Cold Spring Harbor, N.Y., 2000 ("Sambrook"), and Current Protocols in Molecular Biology, F. M. Ausubel et al., eds., John Wiley & Sons, Inc., (supplemented through 2002), each of which is expressly incorporated by reference herein.

In vectors for use in practicing the invention, the heterologous nucleic acid coding sequence or gene for a cytokine or costimulatory molecule is operably linked to a promoter that is capable of driving expression of the coding sequence or gene. A coding sequence or gene is "operably linked" when the promoter is capable of directing transcription of the coding sequence or gene. A "gene" is any nucleic acid sequence coding for a protein or mRNA molecule. A gene comprises coding sequences and non-coding (e.g., regulatory) sequences, while a "coding sequence" is limited to coding DNA. A "promoter" is a DNA sequence that directs the binding of RNA polymerase and thereby promotes RNA synthesis. "Enhancers" are cis-acting elements of DNA that stimulate or inhibit transcription of adjacent genes. All proper transcription, translation and processing signals (e.g., splicing and polyadenylation signals) are correctly arranged on the vector such that the cytokine or costimulatory molecule gene or coding sequence is appropriately transcribed and translated in the cell into which it is introduced. The construction of such vectors for effective expression in host cells is well within the knowledge of the ordinary skilled artisan.

As used herein, a cytokine or costimulatory molecule gene or coding sequence includes genomic or cDNA sequences, variant sequences and mutations thereof, whether isolated from nature or synthesized in whole or in part, so long as the gene or coding sequence can express a protein having the characteristic function of the cytokine costimulatory molecule. The means of modifying genes or coding sequences are well-known in the art.

Any vector can be employed that is suitable for introduction of nucleic acids into eukaryotic cells, or more particularly animal cells, such as mammalian, e.g., human, cells. Preferably, the vector is compatible with the cell, e.g., is capable of effecting expression of the cytokine or costimulatory gene or coding sequence in the cell. Exemplary vectors for use in practicing the invention include, but are not limited to, viruses, plasmids, retrotransposons, cosmids and/or the like. Viral vectors include, but are not limited to, parvovirus vectors, herpes virus vectors, retrovirus vectors, adenovirus vectors, lentiviral vectors, and the like. Alone, or in combination with viral vectors, a number of non-viral vectors are also useful for introducing (e.g., transfecting) heterologous nucleic acid coding sequences for a cytokine or costimulatory molecule into cells. Suitable non-viral vectors include, but are not limited to, plasmids, cosmids, and phagemids, liposomes, water-oil emulsions, polethyteneimines, biolistic pellets/beads, and dendrimers.

In one aspect of the invention, ex vivo methods are employed wherein a plurality of cells are taken from an individual, a heterologous nucleic acid coding sequence or gene for a cytokine or costimulatory molecule is introduced into the cells in a manner effective to express the cytokine or costimulatory molecule, as further described above.

Ex vivo methods are typically employed with cells that are autologous or allogeneic. A heterologous nucleic acid coding sequence or gene for a cytokine or costimulatory molecule may be introduced into such autologous or allogeneic cells, followed by expression thereof, resulting in production of a recombinant live cancer cell. The autologous or allogeneic recombinant live cancer cell can be frozen using the cryoprotective medium and methods described herein. When thawed, the recombinant live cancer cells can be administered to a patient as a cellular vaccine.

Bystander cells are cells that lack major histocompatibility class I (MHC-I) antigens and major histocompatibility class II (MHC-II) antigens on their surface and hence find use as a universal cytokine or costimulatory molecule-producing cell line. A heterologous nucleic acid coding sequence or gene for a cytokine or costimulatory molecule may be introduced into such bystander cells, followed by expression thereof, resulting in production of a recombinant live bystander cell line. The bystander cell line can be frozen with the cryoprotective medium and methods described herein. When thawed, the recombinant bystander cells can be administered to a patient as a cellular vaccine. The use of bystander cells in active immunotherapy is described in U.S. Pat. No. 6,464,973, expressly incorporated by reference herein.

The recombinant live cancer cells can be cultured in conventional nutrient media modified as appropriate to the particular cell type. Culture methods and modifications thereof are well within the knowledge of those of skill in the art. References for cell isolation and culture include Freshney (2000) Culture of Animal Cells, a Manual of Basic Technique, fourth edition, Wiley-Liss, New York and the references cited therein; Payne et al. (1993) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media, second edition (1997) CRC Press, Boca Raton, Fla.

Kits

Kits for preserving the viability of recombinant live cancer cells are also included in the invention. In one aspect, a kit of the invention includes: a container containing a cryoprotective medium comprising about 5% by weight to about 22% by weight hydroxyethyl starch (HES) or derivative thereof alone or in combination with about 1% by weight to about 15% by weight DMSO, and, optionally, from about 0 to about 10% human serum albumin (HSA), and instructional materials teaching the use of the cryoprotective medium to preserve cell viability. In another aspect, a kit of the invention includes: a container containing a cryoprotective medium comprising about 5% by weight to about 15% by weight hydroxyethyl starch (HES) or derivative thereof alone or in combination with about 1% by weight to about 10% by weight DMSO, and, optionally, from about 0 to about 10% human serum albumin (HSA), and instructional materials teaching the use of the cryoprotective medium to preserve cell viability. In yet another aspect, a kit of the invention includes: a container containing a cryoprotective medium comprising about 5% by weight to about 10% by weight hydroxyethyl starch (HES) or derivative thereof alone or in combination with about 1% by weight to about 6% by weight DMSO, and, optionally, from about 0 to about 10% human serum albumin (HSA), and instructional materials teaching the use of the cryoprotective medium to preserve cell viability.

A kit can also include a container containing a cryoprotective medium comprising about 5% by weight to about 22% by weight hydroxyethyl starch (HES) or derivative thereof, about 3% by weight to about 15% by weight glycerol, and, optionally, from about 0 to about 10% human serum albumin (HSA), and, instructional materials teaching the use of the cryoprotective medium to preserve cell viability. In another embodiment, a kit can also include a container containing a cryoprotective medium comprising about 5% by weight to about 15% by weight hydroxyethyl starch (HES) or derivative thereof, about 3% by weight to about 10% by weight glycerol, and, optionally, from about 0 to about 10% human serum albumin (HSA), and, instructional materials teaching the use of the cryoprotective medium to preserve cell viability. In yet another embodiment, a kit can also include a container containing a cryoprotective medium comprising about 5% by weight to about 10% by weight hydroxyethyl starch (HES) or derivative thereof, about 3% by weight to about 6% by weight glycerol, and, optionally, from about 0 to about 10% human serum albumin (1-ISA), and, instructional materials teaching the use of the cryoprotective medium to preserve cell viability.

The HES in the kit can include a variety of molecules as described herein. In one embodiment, HES includes HES, which is, e.g., (a) etherified with hydroxyethyl groups wherein the degree of molecular substitution is about 0.70; (b) etherified with hydroxyethyl groups, wherein the degree of molecular substitution is from about 0.4 to about 0.6; or a combination of (a) and (b). In another embodiment, HES includes a molecule with, e.g., (a) a molecular weight of from about 420 to about 480 kDa; (b) a molecular weight of from about 200 to about 290 kDa; or a combination of (a) and (b).

The instructional material can be affixed to the packaging material or can be included as a package insert. While the instructional material typically comprise written or printed materials they are not limited to such. Any medium capable of storing such instructional material and communicating them to an end user is contemplated by this invention. Such media include, but are not limited to, electronic storage media (e.g., magnetic discs, tapes, cartridges, chips), optical media (e.g., CD ROM), and the like. As used herein, the term "instructional material" can include the address of an internet site that provides the instructions.

The following examples are offered to illustrate, but not to limit the claimed invention.

EXAMPLE 1

Viability and Cytokine Production Following Freezing and Thawing of Recombinant Live Cancer Cells The present invention provides formulations and methods for the cryopreservation of recombinant live cancer cells. The cells may be autologous, allogeneic or bystander cells. The formulations and methods described herein are applicable to all three types of recombinant live cancer cells. In developing the methods and formulations described herein, the allogeneic human prostate tumor cell line, LNCaP, was cultured under standard condition, pelleted and resuspended in a number of different cryoprotective media. LNCaP cells were suspended in each cryoprotective medium, frozen to −80.degree. C., then thawed in a 37.degree. C. water bath, washed with culture medium. Viability was evaluated microscopically by hemacytometer using the trypan-exclusion method. FIG. 1 is a graph showing the % viability of LNCaP cells before (pre-freeze), immediately after (initial thaw) and 24 hours after the cells were suspended in cryoprotective media, frozen to −80.degree. C. and thawed at 37.degree. C. Viability of greater than about 60% was maintained when the cryoprotective media included HES (either Hetastarch or Pentastarch) together with 5% glycerol and 5% HSA in PBS.

Figures 2A, 2B:
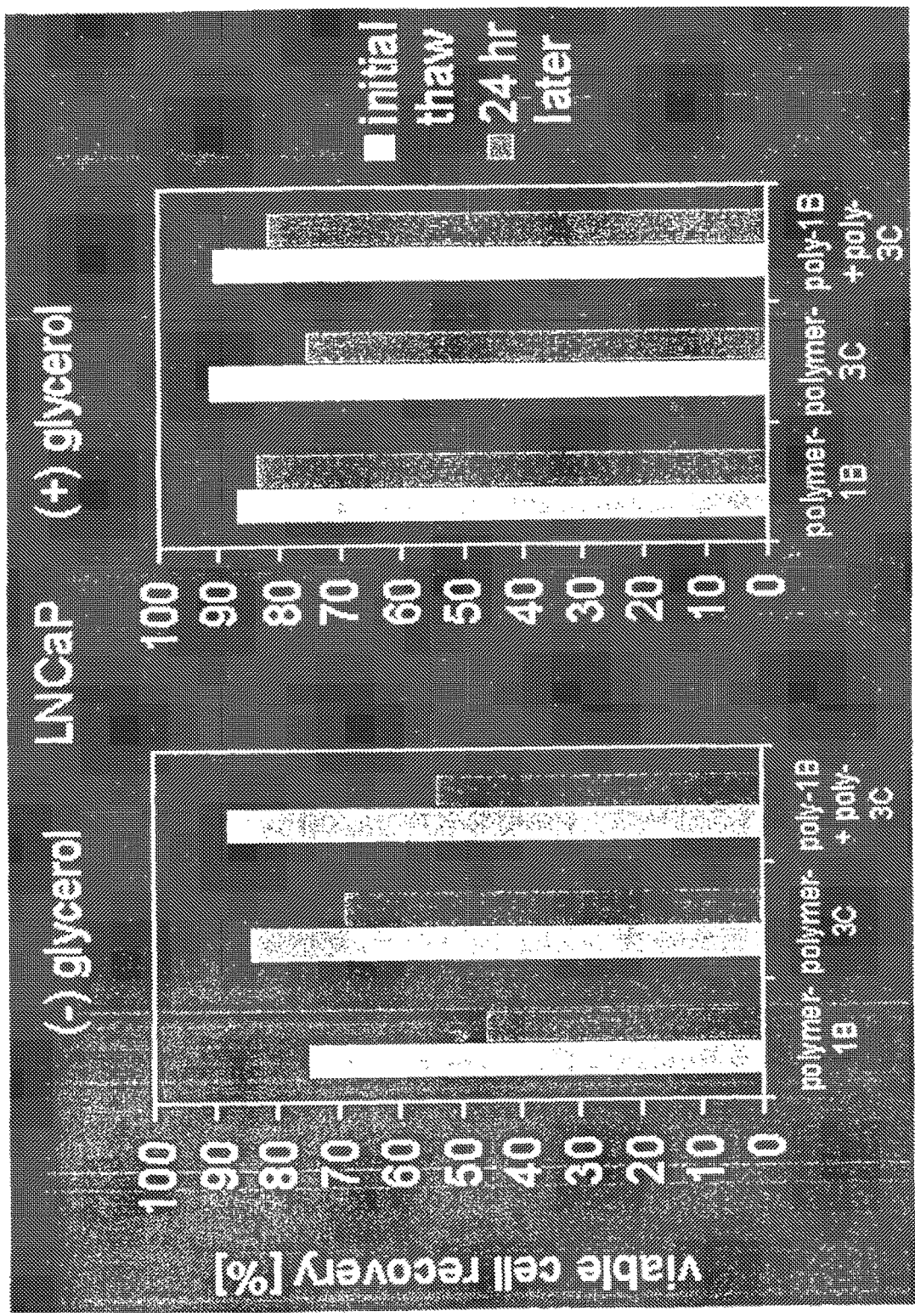
FIG. 2A is a graph showing the viable cell recovery (% viability) of LNCaP cells either immediately following freezing at −80° C. and thawing at 37° C. (initial thaw) or 24 h after thawing (24 hr later). The LNCaP cells were suspended in cryoprotective media comprising polymer 1B (20% HES) alone with or without a second polymer.
FIG. 2B is a graph showing the viable cell recovery (% viability) of LNCaP cells either immediately following freezing at −80° C. and thawing at 37° C. (initial thaw) or 24 h after thawing (24 hr later). The LNCaP cells were suspended in cryoprotective media comprising polymer 1B (20% HES) plus 5% glycerol with or without a second polymer.
Figures 3A, 3B:
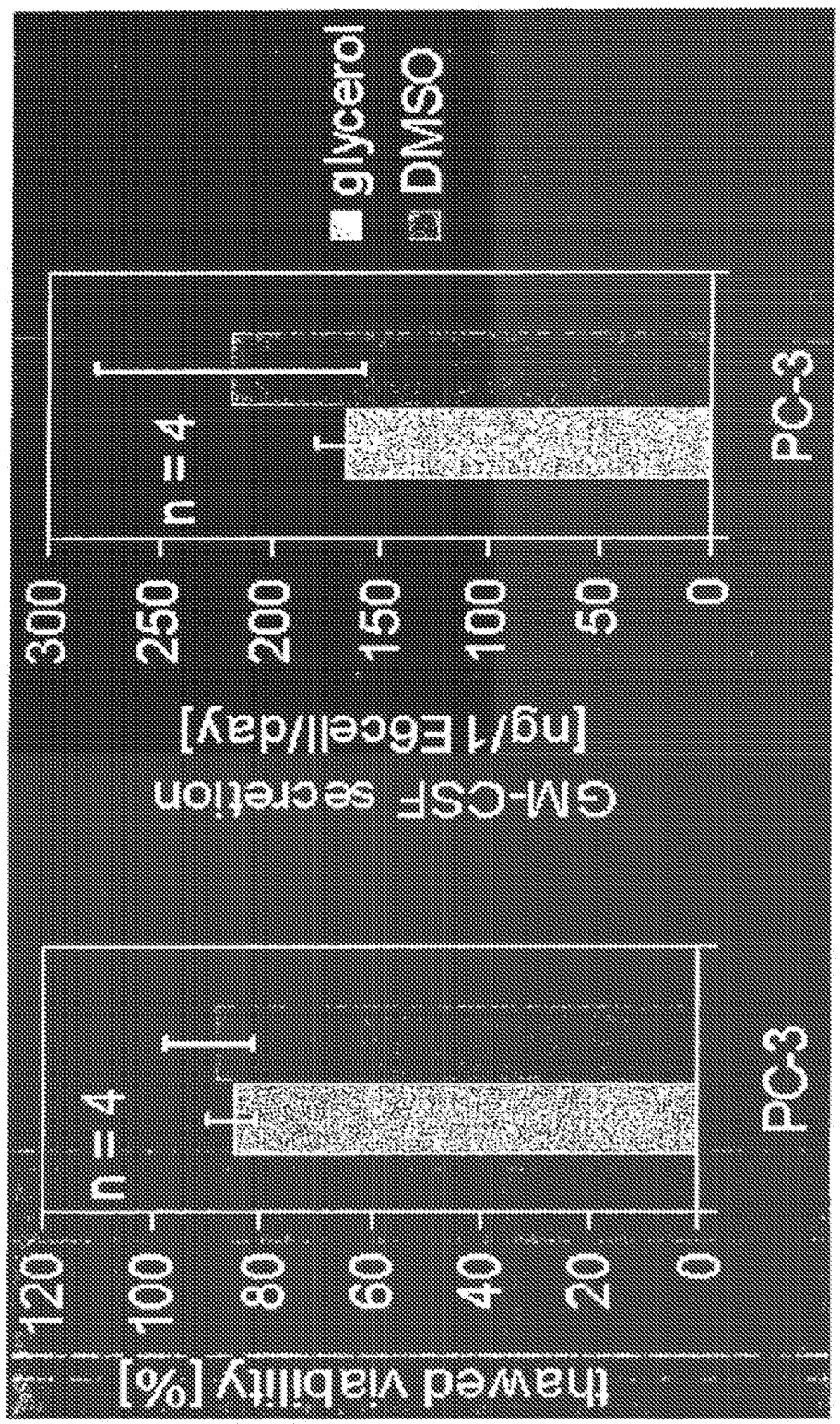
FIG. 3A is a graph showing the % viability of several independently produced cultures of PC-3 cells, each of which was suspended in 20% HES+5% DMSO or 5% glycerol, frozen to −80° C., then thawed at 37° C.
FIG. 3B is a graph showing GM-CSF secretion of several independently produced cultures of PC-3 cells, each of which was suspended in 20% HES+5% DMSO or 5% glycerol, frozen to −80° C., then thawed at 37° C.

The viability of LNCaP cells following suspension in polymer 1B (20% HES) with and without 5% glycerol and with or without a second polymer was evaluated microscopically by hemacytometer using the trypan-exclusion method. The suspensions were frozen to −80.degree. C., thawed in a 37.degree. C. water bath, washed with culture medium, then viability was evaluated immediately upon thawing at 37.degree. C. and 24 h later. The LNCaP cells were suspended in cryoprotective media comprising polymer 1B (20% HES) alone with or without a second polymer (FIG. 2A) or polymer 1B (20% HES) plus 5% glycerol and with or without a second polymer (FIG. 28). Viability of greater than about 60% was maintained upon initial thaw and 24 hours later in each case where 20% HES was used in combination with 5% glycerol in the cryoprotective media. The viability and GM-CSF secretion of several independently produced cultures of PC-3 prostate adenocarcinoma cells was evaluated following suspension in 20% HES+5% DMSO or glycerol, and freezing at −80.degree. C. The frozen cell suspensions were thawed in a 37.degree. C. water bath, washed with culture medium, then viability was evaluated. One million of the medium-suspended cells were seeded into a culture flask and allowed to attach over 24 hr. At 24 hr, the medium was replaced. At 48 hr, the medium was collected and measured for GM-CSF concentration by ELISA. The amount of secreted GM-CSF was normalized to a secretion rate per million cells. The % viability of the PC-3 cells is shown in FIG. 3A and GM-CSF secretion by the cells is shown in FIG. 3B. Greater than 80% viability was maintained when either DMSO or glycerol was used in the cryoprotective media and a GM-CSF secretion level of greater than 150 ng/10.sup.6 cells/day was observed in each case.

Figures 4A, 4B:
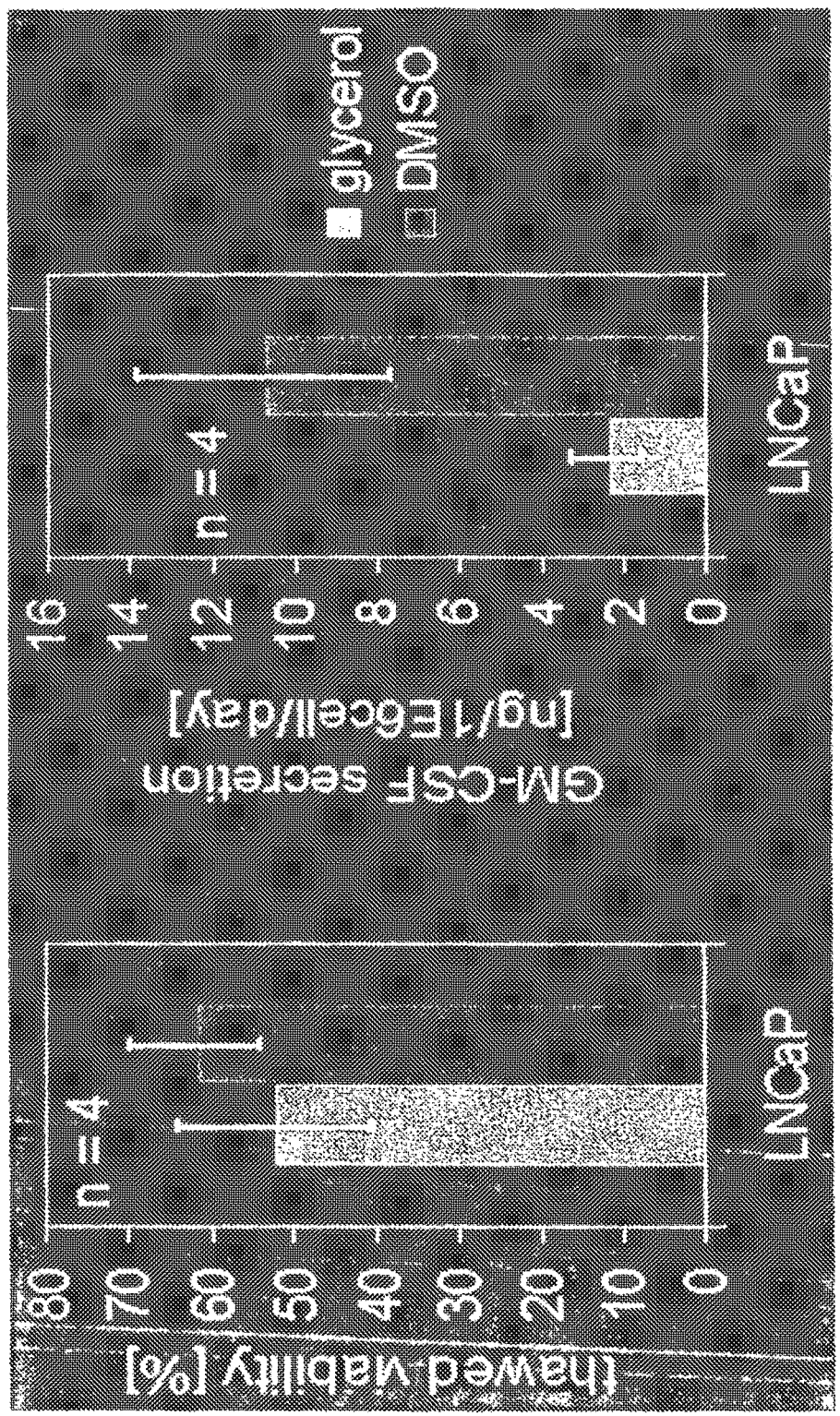
FIG. 4A is a graph showing the % viability of several independently produced cultures of LNCaP cells, each of which was suspended in 20% HES+5% DMSO or glycerol, frozen at −80° C., then thawed at 37° C.
FIG. 4B is a graph showing GM-CSF secretion of several independently produced cultures of LNCaP cells, each of which was suspended in 20% HES+5% DMSO or glycerol, frozen at −80° C., then thawed at 37° C.

The viability and GM-CSF secretion of several independently produced cultures of LNCaP cells was evaluated following suspension in 20% HES+5% DMSO or glycerol, and freezing at −80.degree. C. The frozen cell suspensions were thawed in a 37.degree. C. water bath, washed with culture medium, then viability was evaluated. One million of the medium-suspended cells were seeded into a culture flask and allowed to attach over 24 hr. At 24 hr, the medium was replaced. At 48 hr, the medium was collected and measured for GM-CSF concentration by ELISA. The amount of secreted GM-CSF was normalized to a secretion rate per million cells. The % viability of the LNCaP cells is shown in FIG. 4A and GM-CSF secretion by the cells is shown in FIG. 4B. Greater than 60% viability was maintained and a GM-CSF secretion level of greater than 10 ng/10.sup.6 cells/day was detected when DMSO was used in the cryoprotective media.

Figure 5:
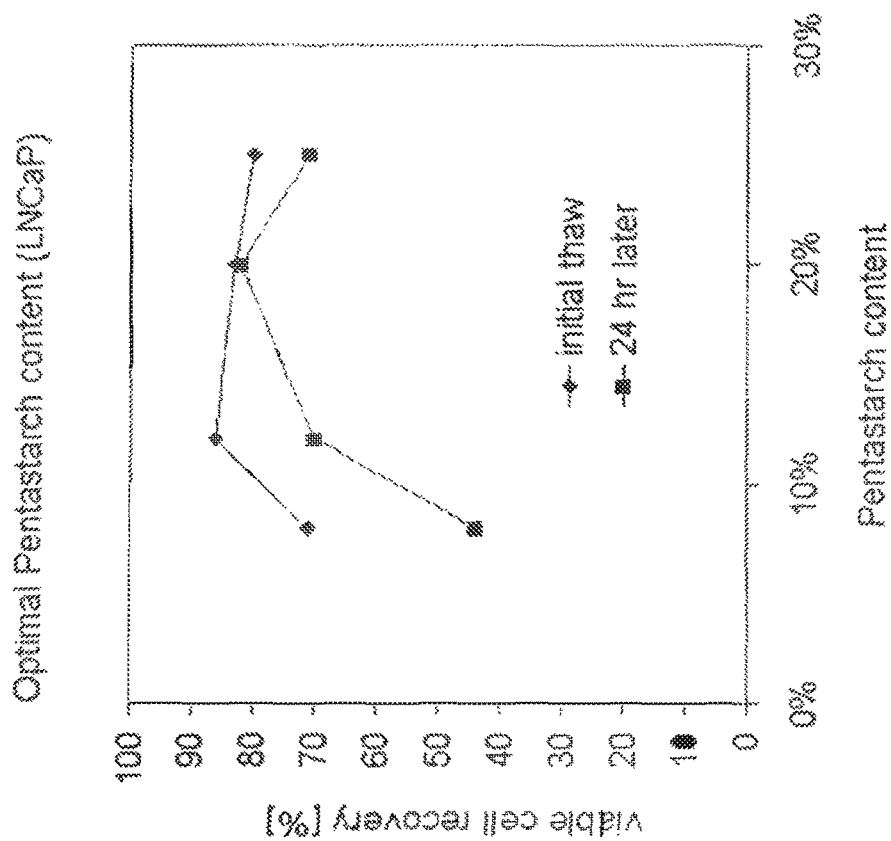
FIG. 5 is a graph showing the % viable cell recovery of LNCaP cells immediately following freezing at −80.degree. C. and thawing at 37.degree. C. or 24 h after thawing. The cells were frozen in cryoprotective medium comprising from 8% to 26% HES and 5% glycerol in PBS.

In a further study, LNCaP cells were suspended in individual cryoprotective media containing 5% glycerol in PBS and from 8% to 26% HES, respectively, then frozen at −80.degree. C. The frozen cell suspensions were thawed in a 37.degree. C. water bath, washed with culture medium, then viability was evaluated. The cells were then seeded into a flask with cell culture medium. After 24 hr, the cells were collected and measured for viability. FIG. 5 is a graph showing the % viable cell recovery of the LNCaP cells immediately following thawing at 37.degree. C. (initial thaw) and 24 h later. The results show that greater than 60% viability was maintained when 5% glycerol and from about 10% to 26% HES (Pentastarch) was included in the cryoprotective media.

EXAMPLE 2

Figure 6A:
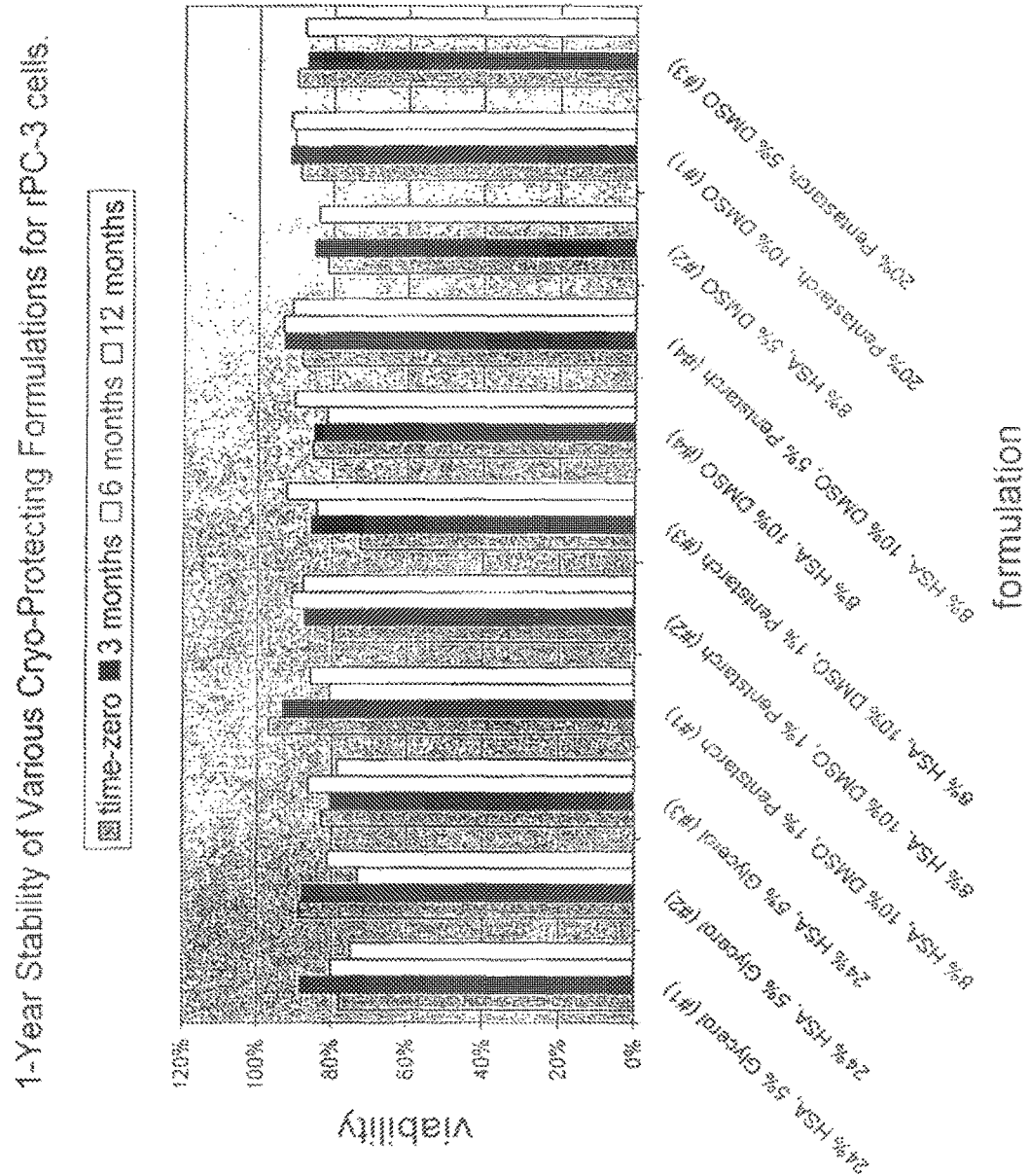
FIG. 6A is a graph showing the % viability of PC-3 cells in a variety of cryoprotective media at time-zero (the time of freezing) and after 3 months, 6 months and 12 months storage at −80.degree. C. The formulations tested are indicated in the figure.
Figure 6B:
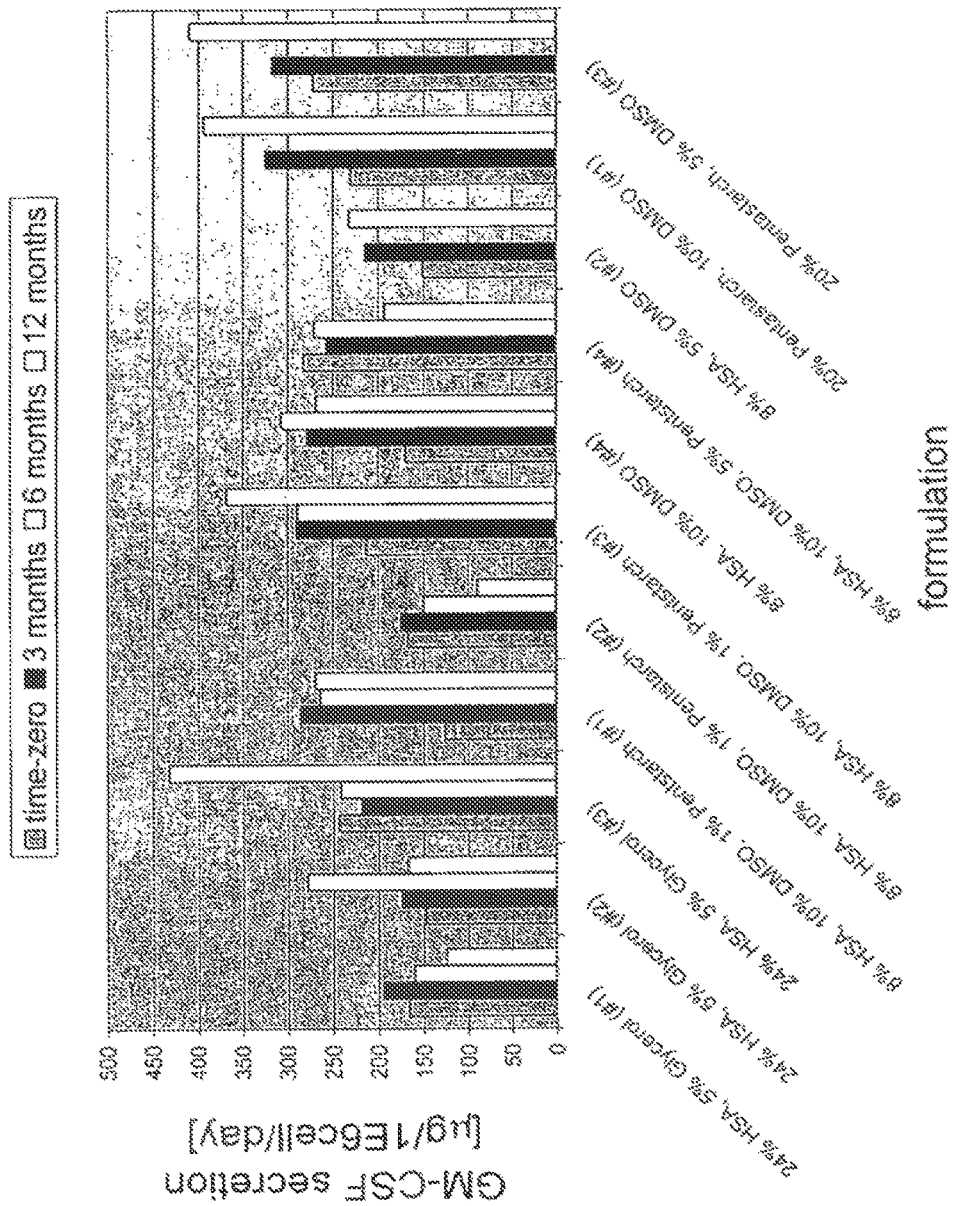
FIG. 6B is a graph showing the GM-CSF secretion by PC-3 cells at time-zero (the time of freezing) and after 3 months, 6 months and 12 months storage at −80.degree. C. in a variety of cryoprotective media. The formulations tested are indicated in the figure.

Viability and Cytokine Production Following Long Term Freezing and Thawing of Recombinant Live Cancer Cells The effect of various cryoprotective media on viability and GM-CSF production by recombinant PC-3 cells was evaluated at time-zero (the time of freezing) and after 3 months, 6 months and 12 months storage at −80.degree. C., respectively. The formulations tested included 24% human serum albumin (HSA), 5% glycerol; 8% HSA, 10% DMSO, 1% Pentastarch; 8% HSA, 10% DMSO; 8% HSA, 10% DMSO, 5% Pentastarch; 8% HSA, 5% DMSO; 20% Pentastarch; 10% DMSO; and 20% Pentastarch, 5% DMSO. At intervals over the 1 year of storage, the frozen cell suspensions were thawed in a 37.degree. C. water bath, washed with culture medium, then measured for viability. One million of the medium-suspended cells were seeded into a culture flask and allowed to attach over 24 hr. At 24 hr, the medium was replaced. At 48 hr, the medium was collected and measured for GM-CSF concentration by ELISA. The amount of secreted GM-CSF was normalized to a secretion rate per million cells. The % viability of the cells is shown in FIG. 6A and GM-CSF secretion by the cells is shown in FIG. 6B. Greater than 60% viability was maintained with each cryoprotective media tested. The most consistent GM-CSF secretion over time was detected when 5 or 10% DMSO was used in combination with Pentastarch with or without HSA in the cryoprotective media (greater than 200 rig GM-CSF/10.sup.6 cells/day).

All publications, patents, and patent applications cited herein are hereby incorporated by reference in their entirety for all purposes. While this invention has been described with an emphasis upon preferred embodiments, it will be obvious to those of ordinary skill in the art that variations of the preferred embodiments can be used and that it is intended that the invention be practiced otherwise than as specifically described herein. Accordingly, this invention includes all modifications encompassed within the spirit and scope of the invention as defined by the following claims.

The invention claimed is:

1. A frozen population of recombinant cancer cells, wherein
the recombinant cancer cells are frozen in a medium comprising about 5% by weight to about 22% by weight of a hydroxyethyl starch (HES) and about 5% by weight to about 10% by weight of DMSO,
wherein the recombinant cancer cells are irradiated prior to freezing or in the cryogenic frozen state to render the recombinant cancer cells proliferation-incompetent; and
wherein the recombinant cancer cells express an introduced heterologous nucleic acid coding sequence for granulocyte-macrophage colony stimulating factor (GM-CSF).

2. The frozen population of claim 1, wherein the medium further comprises from about 0% by weight to about 10% by weight human serum albumin (HSA).

3. The frozen population according to claim 2, wherein the medium comprises about 8% by weight HES, about 2% by weight HSA, and about 5% by weight DMSO.

4. The frozen population according to any one of claims 1-3, wherein the HES comprises HES: (a) etherified with hydroxyethyl groups wherein the degree of molecular substitution is from about 0.60-0.80; (b) etherified with hydroxyethyl groups, wherein the degree of molecular substitution is from about 0.40-0.60; or a combination of (a) and (b).

5. The frozen population according to claim 4, wherein the HES comprises HES: (a) etherified with hydroxyethyl groups wherein the degree of molecular substitution is about 0.70; (b) etherified with hydroxyethyl groups, wherein the degree of molecular substitution is from 0.4 to about 0.5; or a combination of (a) and (b).

6. The frozen population according to claim 5, wherein the HES comprises HES with: (a) a molecular weight of from about 420 to about 480 kDa; (b) a molecular weight of from about 200 to about 290 kDa; or a combination of (a) and (b).

7. The frozen population according to claim 1, wherein the recombinant cancer cells express an additional cytokine or a costimulatory molecule.

8. The frozen population according to any one of claims 1-7, wherein the recombinant cancer cells are selected from the group consisting of lung cancer cells, pancreatic cancer cells, prostate cancer cells, kidney cancer cells, myeloma cells, and leukemic cells.

9. The frozen population according to claim 8, wherein the the recombinant cancer cells comprise patient-derived cells.

10. The frozen population according to claim 8, wherein said recombinant cancer cells are autologous, allogeneic or bystander cells.

11. The frozen population according to claim 2, wherein the HES comprises HES: (a) etherified with hydroxyethyl groups wherein the degree of molecular substitution is from about 0.60-0.80; (b) etherified with hydroxyethyl groups, wherein the degree of molecular substitution is from about 0.40-0.60; or a combination of (a) and (b).

12. The frozen population according to claim 3, wherein the HES comprises HES: (a) etherified with hydroxyethyl groups wherein the degree of molecular substitution is from about 0.60-0.80; (b) etherified with hydroxyethyl groups, wherein the degree of molecular substitution is from about 0.40-0.60; or a combination of (a) and (b).

* * * * *